United States Patent
Yeh

(10) Patent No.: US 6,843,964 B2
(45) Date of Patent: Jan. 18, 2005

(54) AIR PURIFYING CAP

(76) Inventor: Kuo-Chung Yeh, No. 149, Sec. 3, Lung Kang Road, Chung-Li City (TW)

( * ) Notice: Subject to any disclaimer, the term of this patent is extended or adjusted under 35 U.S.C. 154(b) by 0 days.

(21) Appl. No.: 10/458,319

(22) Filed: Jun. 11, 2003

(65) Prior Publication Data

US 2004/0258576 A1 Dec. 23, 2004

(51) Int. Cl.$^7$ ................................................ A62B 7/08
(52) U.S. Cl. ........................ 422/121; 2/171.2; 361/232; 422/123
(58) Field of Search ................................. 422/120, 121, 422/123; 361/230, 232; 2/171.3, 8, 10, 410, 422, 171.2

(56) References Cited

U.S. PATENT DOCUMENTS

| | | | | |
|---|---|---|---|---|
| 4,680,815 A | * | 7/1987 | Hirsch et al. ................. 2/171.3 |
| 5,425,620 A | * | 6/1995 | Stroud ........................... 416/63 |
| D396,340 S | * | 7/1998 | She ............................... D2/876 |
| 5,861,127 A | * | 1/1999 | Yeh ............................. 422/121 |
| 6,419,171 B1 | * | 7/2002 | Takayanagi ................. 239/690 |

* cited by examiner

Primary Examiner—Krisanne Jastrzab
(74) Attorney, Agent, or Firm—Troxell Law Office PLLC

(57) ABSTRACT

An air-purifying cap comprises a main body and an anion generator. The main body has a groove at the front cap edge to accommodate the anion generator. The anion generator is a box incorporating a high voltage circuit and a battery, or a box attached with a solar energy collecting plate, so the battery or the solar energy plate can supply DC power to high voltage circuit and allow the internal discharge electrode for high voltage discharge to produce huge amount of anions that output from the box bottom. The released anions will decompose airborne virus and purify the air quality for human respiratory system. It provides an instant measure to effectively inhibit the spreading virus.

3 Claims, 5 Drawing Sheets

AIR PURIFYING CAP

FIELD OF THE INVENTION

The present invention is related to a cap, especially an air-purifying cap that incorporates an anion generator to properly purify the ambient air.

BACKGROUND OF THE INVENTION

In the industrialized society, population becomes increasingly dense. Contamination sources and virus using air as medium always surround us. As a result, allergy, asthma, headache, flu and all kinds of discomfort take place. Current epidemic SARS is an example. If we fail to purify suspending virus and suspending particles around us, they may get into human body through air transmission and severely harm our health.

SUMMARY OF THE INVENTION

The main objective for the present invention is to solve the problem with air contamination sources and virus to get into human body through air media. An air-purifying cap is invented to generate anions with portability. The anions suspending around human respiratory system to purify the surrounding air and provide a health caring measure by effectively inhibiting the spreading virus.

BRIEF DESCRIPTIONS OF THE INVENTION

DETAILED DESCRIPTION OF THE INVENTION

Figure 1:
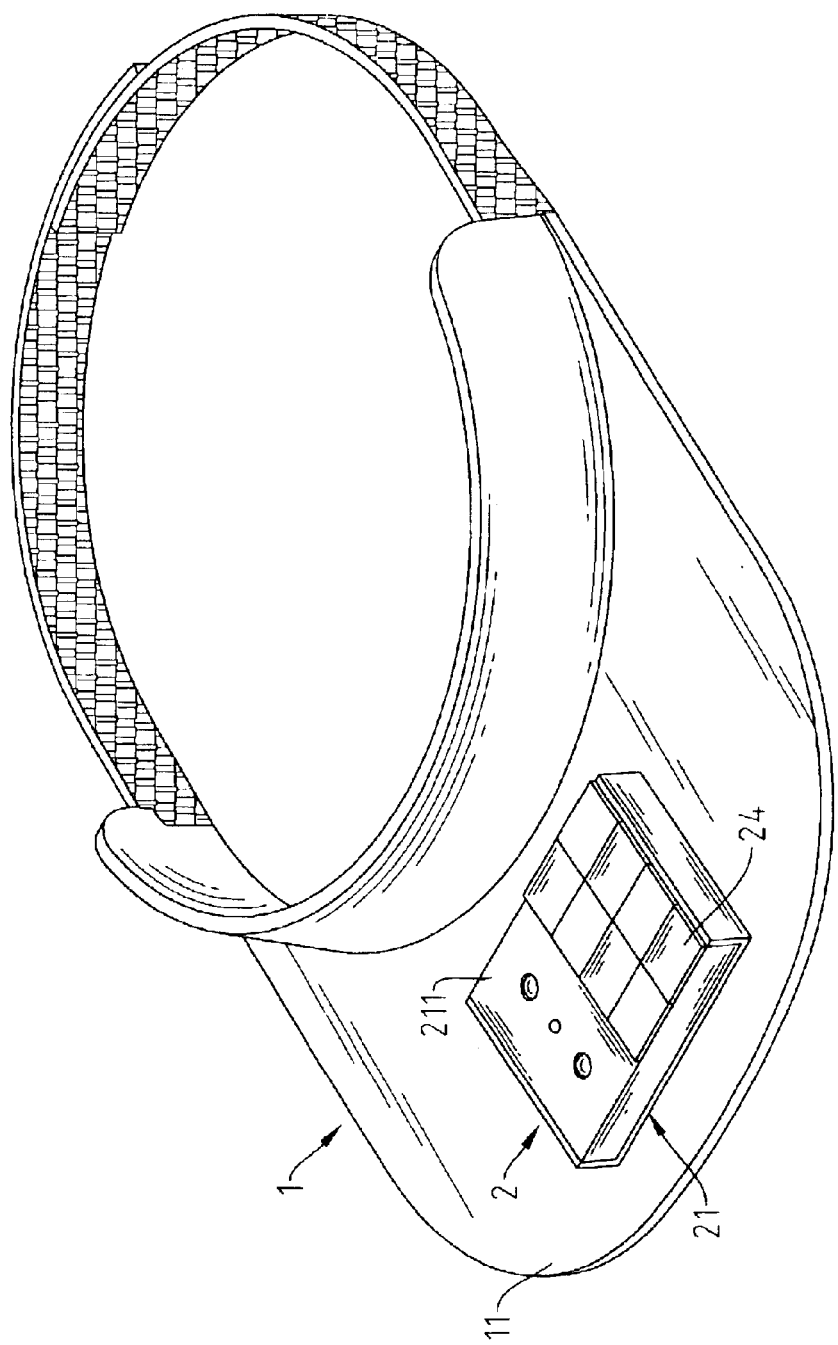
FIG. 1 is an illustration for the appearance for the present invention.
Figure 2:
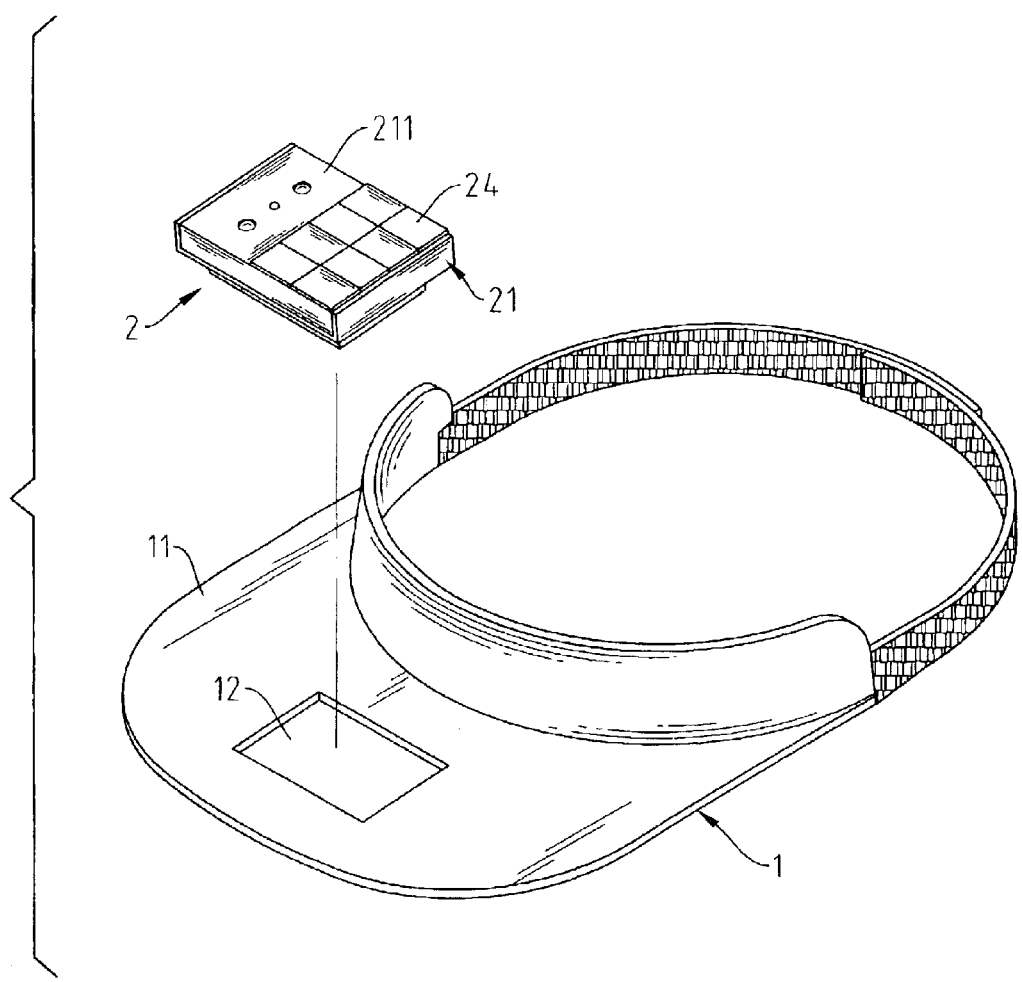
FIG. 2 is the illustration for the decomposition diagram for the components of the present invention.

Please refer to FIG. 1 and FIG. 2. The present invention comprises a main body 1 and an anion generator 2. The main body 1 has a groove 12 at the front cap edge 11 to accommodate the anion generator 2. The anion generator 2 is a box 21 incorporating a high voltage circuit 22 and a battery 23, or a box 21 attached with a solar energy collecting plate 24.

Figure 3:
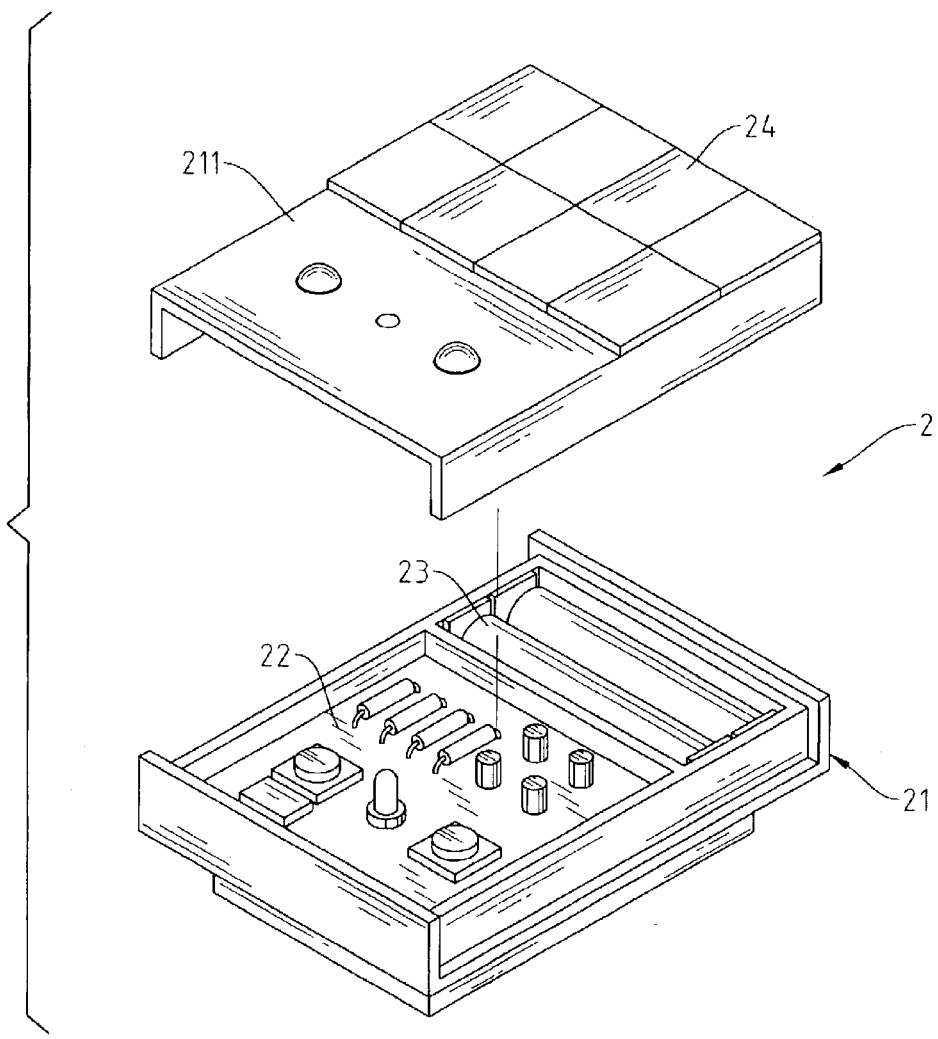
FIG. 3 is the internal mechanism for the anion generator for the present invention.

The above-mentioned high voltage circuit 22 uses DC power (1.5V, 3V or 9V) directly supplied by the battery 23 or the solar energy collecting plate 24. When battery 23 power is out, the top cover 211 of the box 21 can be open to replace the battery 23 (as in FIG. 3), or without replacing the battery 23, the solar energy collecting plate 24 is directly exposed to outside to provide DC power. Thus, the power for the anion generator 2 will not be interrupted. The anion generator 2 is capable of long term operation, so the user carrying the anion generator 2 can have surrounding air constantly purified by the anions. The present invention possesses practical value and progressiveness.

Figure 4:
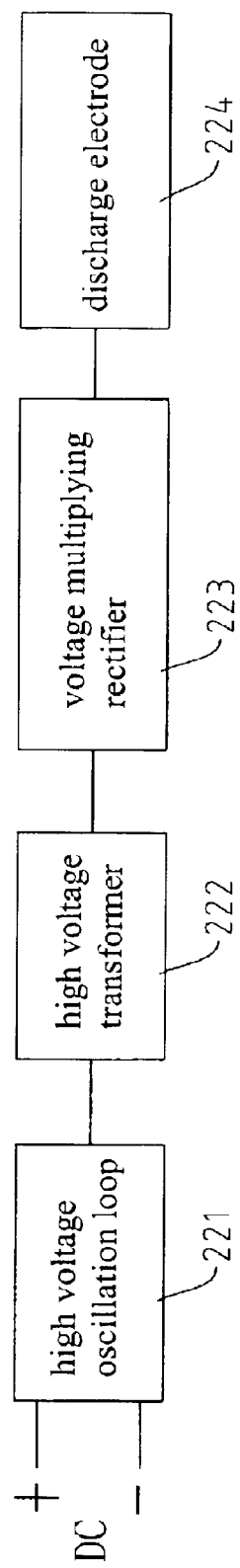
FIG. 4 is the block diagram for the operation of high voltage circuit to produce high voltage pulse current for the present invention.
Figure 5:
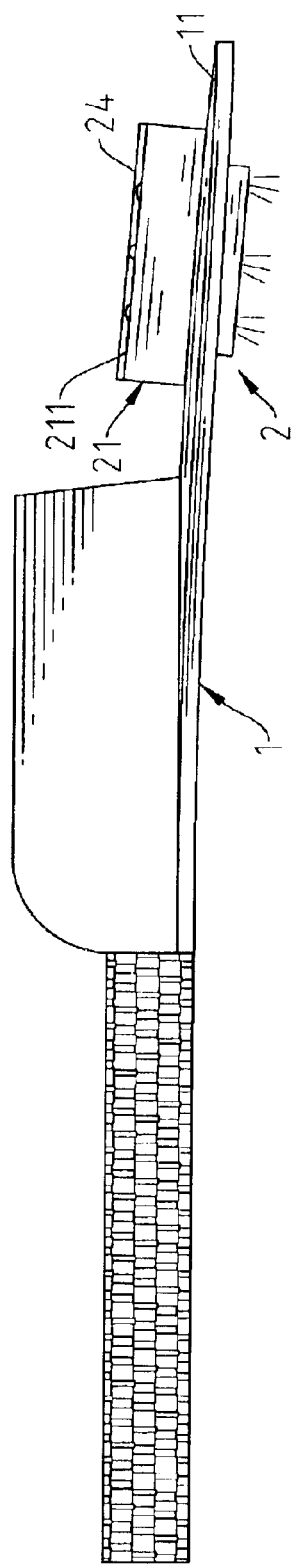
FIG. 5 is an embodiment for the present invention.

Hence, in a practical operation, the present invention uses the battery 23 or the solar energy collecting plate 24 exposed outside the main body 1 to supply DC power (1.5V, 3V or 9V) to the high voltage circuit 22. Through an oscillation loop 221 inside the high voltage circuit 22, the high voltage transformer 222 and voltage multiplying rectifier 223 output high voltage pulse current to discharge electrode 224 (as in FIG. 4). Therefore, a great amount of anions are produced at the discharge electrode 224 and output through the box bottom 21 (as in FIG. 5). The anions decompose airborne suspending virus and purify the air surrounding human respiratory system. It provides a health care measure by effectively inhibiting the spreading virus.

What is claimed is:

1. An air purifying cap comprising:
    a) a cap shaped body having a hole in a front edge thereof; and
    b) an anion generator located in the hole in the cap shaped body and having:
        i) a box;
        ii) a high voltage circuit located in the box wherein the high voltage circuit includes a high voltage oscillation loop; a high voltage transformer electrically connected to the high voltage oscillating loop; a voltage multiplying rectifier electrically connected to the high voltage transformer; and an electrode electrically connected to the voltage multiplying rectifier; and
        iii) an power source electrically connected to the high voltage circuit, the anion generator producing and releasing a plurality of anions from a bottom of the box and through the hole in the cap shaped body.

2. The air purifying cap according to claim 1, wherein the power source is a battery.

3. The air purifying cap according to claim 1, wherein the power source is a solar energy collecting plate.

* * * * *